(12) United States Patent
Chen

(10) Patent No.: US 8,247,644 B2
(45) Date of Patent: Aug. 21, 2012

(54) METHOD FOR MANUFACTURING ANIMAL MODEL FOR RESEARCHING PULMONARY TUMOR AND USE THEREOF

(75) Inventor: Chuan-Mu Chen, Taichung (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 12/828,786

(22) Filed: Jul. 1, 2010

(65) Prior Publication Data

US 2011/0004950 A1    Jan. 6, 2011

(30) Foreign Application Priority Data

Jul. 2, 2009 (TW) .............................. 98122476 A

(51) Int. Cl.
*A01K 67/033* (2006.01)
*A01K 67/00* (2006.01)
*C12N 15/00* (2006.01)

(52) U.S. Cl. ................................ 800/18; 800/8; 800/21
(58) Field of Classification Search ................ 800/8, 18, 800/21

See application file for complete search history.

(56) References Cited

U.S. PATENT DOCUMENTS

| 6,793,918 B2 * | 9/2004 | Enholm et al. ............... 424/93.2 |
| 2003/0166562 A1 * | 9/2003 | Rothenberg et al. ............ 514/12 |
| 2006/0182736 A1 * | 8/2006 | Kim et al. .................. 424/94.65 |

OTHER PUBLICATIONS

Haruyama et al. Curr Protoc Cel Biol. Mar. 2009. Chapter Unit-19.10. doi:10.1002/0471143030.cb11910s42. pp. 1-12.*

* cited by examiner

*Primary Examiner* — Marcia S Noble
(74) *Attorney, Agent, or Firm* — Ming Chow; Sinorica, LLC

(57) ABSTRACT

The present invention is a method for manufacturing an animal model for researching a pulmonary tumor and a use thereof. A transgenic non-human animal of the present invention is prepared by embryonic gene microinjection and possesses a tissue-specific expression of vascular endothelial growth factor $A_{165}$ (VEGF-$A_{165}$) in lung. Through the expression of vascular endothelial growth factor $A_{165}$, the lung cells in the transgenic non-human animal of the present invention have inflammatory, vascularogenesis and angiogenesis responses or induce lung tumors. Thus, the non-human animal of the present invention can serve as an animal model for analyzing the regulation and the anti-tumor drugs screening of pulmonary adenocarcinoma.

6 Claims, 10 Drawing Sheets

Human VEGF-A₁₆₅ Antibody

SEQUENCE LISTING

<160> NUMBER OF SEQ ID NOS: 2

<210> SEQ ID NO 1
<211> LENGTH: 585
<212> TYPE: DNA
<213> ORGANISM: mouse
<220> FEATURE:
<221> NAME/KEY: misc_feature
<222> LOCATION: (40)..(40)
<220> FEATURE:
<221> NAME/KEY: misc_feature
<222> LOCATION: (40)..(40)
<223> OTHER INFORMATION: n is a, c, g, or t

<400> SEQUENCE: 1

```
cgtaggaaca ggccaacctt gcctgatcta ggccctgggn tctctgatgt gtactatgga      60
gaagtctttc tatgttcacg tctactgtat gtaggatcga gcctgtctaa caatgcccaa     120
gaatcgagtg accttgtggc ttgaagtcta gccacgttcg ttggagggag gcaatagaag     180
gagtctagtg acatctcaga gtcctgtgtc tttgtccttc cctgtgattc ctgaagggtc     240
tccggcctct ggttctccag ggttggcaag tctacagttg cttcctggaa cctggagtgc     300
tcagtgcttg acttccaaga gaggacacag ttgtcttcta cagttccacg acctctgact     360
tgggtcctcc actgcctgaa tactccacaa gtggcctatt gtgtgagtga gctcagtttc     420
aatgggaaca gaaactgggt ttatgaaaag agattatttg cttattccac ggagaagatg     480
accaagtaaa taatgcaatc tcctaagtgg agcgcaatca ctgccctcta cctcttgtgg     540
gctgcaagga acatataaaa agccacacac ccacacatac ccaca                     585
```

<210> SEQ ID NO 2
<211> LENGTH: 576
<212> TYPE: DNA
<213> ORGANISM: human
<220> FEATURE:
<221> NAME/KEY: gene
<222> LOCATION: (1)..(576)

<400> SEQUENCE: 2

```
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240
```

-continued

```
atgcgatgcg ggggctgctg caatgacgag ggcctggagt gtgtgcccac tgaggagtcc    300
aacatcacca tgcagattat gcggatcaaa cctcaccaag gccagcacat aggagagatg    360
agcttcctac agcacaacaa atgtgaatgc agaccaaaga aagatagagc aagacaagaa    420
aatccctgtg ggccttgctc agagcggaga aagcatttgt ttgtacaaga tccgcagacg    480
tgtaaatgtt cctgcaaaaa cacagactcg cgttgcaagg cgaggcagct tgagttaaac    540
gaacgtactt gcagatgtga caagccgagg cggtga                              576
```

METHOD FOR MANUFACTURING ANIMAL MODEL FOR RESEARCHING PULMONARY TUMOR AND USE THEREOF

BACKGROUND OF THE INVENTION

The present invention relates to an animal model for researching pulmonary tumors, and especially, a transgenic non-human animal is prepared by genetic engineering for providing a tissue-specific expression of vascular endothelial growth factor $A_{165}$ (VEGF-$A_{165}$) in lung cells. Therefore, it is used for establishing an animal model for investigating the therapeutic effects of variable medicines on tumorigenesis of pulmonary adenocarcinoma.

According to the statistics made by the American Cancer Society, cancers have ranked as the second one in the top 10 death cause in America. Especially, lung cancer has become the first one in the top 10 death causing cancers in the past 10 years in America. Briefly, the number of patients dead by lung cancer is about 163,500 in 2005. The number of patients having death cause of lung cancer increases from 89.5 patients in 1975 to 72 patients in 2007 per 100,000 male persons. The number of patients having death cause of lung cancer increases from 24.5 patients in 1975 to 53 patients in 2007 per 100,000 female persons. Taking a view in the whole world, the incidence rate of lung cancer among all cancers is 12.8% and the mortality rate of is up to 90%. It is more amazing that the number of persons dead by lung cancer in 1990 has increased to be 4 times of that in 1950. Till now, the incidence rate of lung cancer has been continued increasing. Thus, there is a need to analyze the induction mechanism of lung cancer in a molecular level so as to propose measures for preventing from it in future.

Lung cancer, according to the bio-characteristics and the clinical manifestation, can be divided into two gross types including small cell lung cancer and non-small cell lung cancer. The non-small cell lung cancer primarily includes pulmonary squamous cell carcinoma, pulmonary large cell lung carcinoma, and pulmonary adenocarcinoma. According to the statistics of epidemiology in Taiwanese district, among patients with lung cancers, the ratio of patients of small cell lung cancer is only 12%-15% and the ratio of patients of non-small cell lung cancer is about 85%-88%. The cells of the small cell lung cancer grow relatively fast and their metastasis probability is higher. Because their reaction rate on chemotherapy and radiation therapy is more than 80%, a systemic chemotherapy for lung cancer prevails over other therapies. On contrast, the cells of the non-small cell lung cancer grow and spread both more slowly. However, only ¼ of early staged patients with the non-small cell lung cancer, through diagnosis, are capable of having an operation and only ¹⁄₁₀ of patients can have an operation to excise the tumor. Further, the metastasis probability or recurring rate of the non-small cell lung cancer in a patient after such an operation is very high. In addition, most patients who are not possible to have an operation are insensible to the chemotherapy and radiation therapy (Lu and, Chang, 1991). Base on the above mentioned, the 5-year survival rate in patients with lung cancer after therapy is only 10%. Pulmonary adenocarcinoma, the most common type of the non-small cell lung cancer (40% of lung cancer) (Travis et al. 1995), induces a tumor resulted from cells classified as secretory cells including clam cell, type II alveolar epithelial cells and mucin producing cells. Pulmonary adenocarcinoma commonly occurs in the peripheral of lung (about ⅔) and the other ⅓ of it starts proliferation from the center of lung (Minna et al., 2002). Upon forming a tumor by pulmonary adenocarcinoma in a patient, it will cause distal metastasis to other organs including brain, kidney, liver, bone and so on in 80% of patients. Therefore, to investigate the mechanism related to the pulmonary adenocarcinoma inducing factors so as to propose measures for preventing from being induced thereby is more important than to cure a tumor after its formation.

The cause of lung cancer primarily consists in gene mutation induced by carcinogens contained in, for example, smoke of long-term cigar addiction or environmentally polluted air. The quantity of gene mutation accumulated for a long term of time may induce cells toward carcinogenesis and promote the growth of a tumor. In addition to cigar addiction, the long-term inflammation response in lung induced by allergens in air may cause the pulmonary adenocarcinoma. Thus, chronic diseases in the lung and family inheritance are two kinds of common cause of pulmonary adenocarcinoma. According to some reports, genetic background is another cause of lung cancers. A person having a family background with lung cancer will have a higher probability in lung carcinomagenesis. From the tests on mice, it is learned that the difference in the carcinogenic probability among mice of variable strains, under treating them with the same dosage of carcinogenic material, is obvious (Minna et al., 2002). In addition, from recent studies of the pulmonary adenocarcinoma, some common gene mutations will lead to the pulmonary adenocarcinoma. A common medicine for treating the pulmonary adenocarcinoma, for example, Geftinib (Iressa), is an anticancer medicine designed on basis of the over-expression characteristics of the epidermal growth factor receptor (EGFR) in the body of patients (Ciardiello et al., 2002; Doroshow, 2005).

The vascular endothelial growth factor (VEGF) is a type of glycoprotein commonly occurring in the form of homodimer, and seldom occurring in the form of heterodimer (Cross et al., 2003). The VEGF plays an important role in embryo development. If it performs abnormally, many diseases will be caused, for example, cardiovascular diseases, pulmonary edema, inflammation response, tumor metastasis, angiogenesis, and so on (Tammela et al., 2004). The VEGF is divided into about four major types, including A, B, C and D types, wherein the VEGF-A is found to be positively relative to the vascular permeability (Connolly et al., 1989; Becker et al., 2005) and it is able to promote the development and differentiation in organs and to promote the vascularogenesis and angiogenesis. Additionally, under normal regulation conditions, VEGF-A is related to help in wounds occlusion and to the regulation in female menstrual cycle (Ferrrara et al., 1997). A cell or a tissue under the status of hypoxia or ischemia is able to induce the expression of the hypoxia-inducible factor-1 (HIF-1) protein increasing, to promote the transcription efficiency of the VEGF-A mRNA, to promote the occurrence of the VEGF-A protein and to cause the angiogenesis. Thus, in the VEGF family, the VEGF-A is the one mostly studied by researchers and medical teams. Further, the VEGF-A is divided into four types of isoforms including VEGF-$A_{121}$, VEGF-$A_{165}$, VEGF-$A_{189}$ and VEGF-$A_{206}$. The VEGF-$A_{165}$, the commonly found type of VEGF-A, primarily functions to promote the angiogenesis. In its gene transcriptant, the exon 6 is spliced and the VEGF-$A_{165}$ still retains the heparin binding site, while its ability to link acetyl heparin sulfate is much lower than that of two isoforms of VEGF-$A_{206}$ and VEGF-$A_{189}$.

The VEGF receptor (VEGFR), a type of cell surface protein, binds with types of the VEGF for inducing an autophosphorylation of the receptor to promote the downstream signals delivery and cause variable physiological reactions. VEGFR is one of receptor tyrosine kinase (RTK) including three types, that is, VEGFR-1, VEGFR-2 and VEGFR-3. The VEGFR-2, also named as KDR or Flk-1, has a high affinity to VEGF-A, VEGF-C and VEGF-D and primarily functions to promote the endothelial cell's survival, hyperplasia and differentiation (Zachary, 2003). If the VEGFR-2 gene knockout vector transfers into a mouse, the mouse will die at the stage of embryogenesis. The dead mouse has a serious defect in term of vascular endothelial cell and haematopoietic precursor. Thus, it is indicated that VEGFR-2 is important to the vascular development (Shalaby et al., 1995). VEGF-A primarily binds to VEGFR-2 and the binding of VEGF-A will induce the VEGFR-2 to form a dimer so as to promote intracellular tyrosine phosphorylation, inducing a series of signals transduction. By using a synthetic drug ZD4190 competitively inhibited the combination of VEGF with VEGFR2, it will effectively block the signals transduction (Gespach et al., 2006). Base on the foregoing, the binding of VEGF-$A_{165}$ and VEGFR2 is very important.

Furthermore, the expression quantity of VEGF-A165 is positively related to the growth and spread of cancer cells. An early staged cancer cells will keep proliferation and thus lead to the deficiency in both the nutrition and oxygen rendering a large amount of cells to die. Therefore, inflammation response will occur and HIF-1α will activate so as to induce a large quantity of VEGF-$A_{165}$ to be secreted. The VEGF-$A_{165}$ will bind the VEGFR2 and thus a downstream signal is activated to induce vasculargenesis (Gasparini, 1999; Ferrara, 2002). It is obvious that the VEGF-$A_{165}$ will help the growth and metastasis in malignant tumor cells. When the cancer cells secret a large amount of VEGF-$A_{165}$, vasculargenesis will be induced so as to provide sufficient nutrition and oxygen to the tumor increasing the tumor growth speed (Ferrara et al., 1997). The over-secretion of VEGF-$A_{165}$ will promote degradation in extra-cellular matrix and increase the vascular permeability rendering that the tumor cells are liable to invade into the tissues (Murphy et al., 1999). Therefore, it is a popular topic to study on developments both in inhibitors and target medicines for the VEGF-$A_{165}$ and related factors of the VEGF-$A_{165}$.

Further, a clara cell is a non-fibrosis lung epidermal cell distributing on the epidermis respectively on bronchus and capillary bronchiole and primarily functions to protect the lung via its performance each in anti-oxidative potential and alleviating inflammation response. The clara cells are capable of secreting a large amount of so-called clara cell secretory protein (CCSP). The CCSP mRNA primarily is found in trachea, bronchus and capillary bronchiole in lung (Hay et al., 1995). Via high oxidative potential tests, it is learned that a mouse with the CCSP gene knockout has a higher level in lung injury and death rate caused by the inflammation response (Johnston et al., 1997). In addition, the CCSP can be used to estimate the marker proteins indicating the lung damage level. In a procedure of acute lung injury, the expression quantities each of the CCSP mRNA and the CCSP in the lung of a mouse treated with ozone will reduce obviously. In addition, the expression of CCSP in the pulmonary adenocarcinom cells is not detected via immunohistochemistry. Thus, in the growth procedure of a tumor, it is deemed that the CCSP functions to inhibit the growth of a tumor (Hicks et al., 2003).

SUMMARY OF THE INVENTION

Base on the foregoing, one aspect of the invention is to provide a method for manufacturing an animal model for researching a pulmonary tumor. The method comprises following steps: (a) constructing an expression vector having a DNA sequence of gene encoding a vascular endothelial growth factor $A_{165}$ (VEGF-$A_{165}$); and (b) introducing the expression vector of the step (a) into a non-human animal embryo by a microinjection process and transplanting the embryo into a female non-human animal so as to enable the embryo to develop into a non-human transgenic animal. The VEGF-$A_{165}$ can express in the lung bronchus epidermal cells of the non-human transgenic animal Furthermore, the expression vector comprises: a 5' regulatory sequence including a clara cell secretory protein (CCSP) promoter can express specific to the lung cells; and a DNA sequence of gene encoding the vascular endothelial growth factor $A_{165}$ (VEGF-$A_{165}$) operably and subsequently connected to the 5' regulatory sequence. Preferably, the non-human animal is a mouse.

Another aspect of the invention is to provide a deoxyribonucleic acid (DNA) construct composed of a transgenic non-human animal genome, comprising a lung cell specific expression promoter; and a DNA sequence of gene encoding a vascular endothelial growth factor A (VEGF-A) operably connected to the subsequence of the lung cell specific expression promoter. Furthermore, the DNA construct preferably binds with a mouse genome so as to enable the VEGF-A to express specifically in its lung cells.

In another aspect of the invention, the present invention provides a transgenic non-human animal for researching a pulmonary tumor. Preferably, the transgenic non-human animal is a mouse whose genome comprises a transgene wherein the transgene includes a lung cell specific expression promoter and a DNA sequence of gene encoding a vascular endothelial growth factor A (VEGF-A) operably and subsequently connected to the lung cell specific expression promoter. The transgene expresses the vascular endothelial growth factor in lung cells of the transgenic non-human animal enabling the lung cells of the transgenic non-human animal to have an inflammation response or to induce a tumor. Thus, it can be used to serve as an animal model for researching the regulatory mechanism of the pulmonary adenocarcinoma. Another aspect of the invention is to provide an animal model for studying on the pulmonary tumors. In this model, a transgenic non-human animal is used to analyze the genesis and regulatory mechanism in pulmonary adenocarcinoma.

DETAILED DESCRIPTION OF THE PREFERRED EMBODIMENTS

The present invention discloses an animal model for researching the pulmonary tumors in which a transgenic non-human animal is enabled to express the vascular endothelial growth factor $A_{165}$ (VEGF-$A_{165}$) specific to its lung. The transgenic non-human animal genome includes a transgene that comprises a lung cell specific expression promoter and a DNA sequence of gene encoding VEGF-A operably and subsequently connected to the promoter. Owing to inflammation response or a tumor occurring in the lung cells of the non-human transgenic animal, such it is used to serve as the animal mode for researching the regulatory and genesis mechanism of pulmonary adenocarcinoma.

Furthermore, the present invention discloses a method for manufacturing an animal model for researching the pulmonary tumors. First, construct an expression vector having a DNA sequence of gene encoding VEGF-$A_{165}$ wherein the expression vector includes a 5' regulatory sequence, i.e., a CCSP promoter, capable of expressing specific to the lung cells; and a DNA sequence of gene encoding VEGF-$A_{165}$ is operably and subsequently connected to the promoter so as to be controlled by the promoter. Then, the expression vector is introducing into an embryo of a non-human animal by a microinjection process and the embryo is transplanted into a female non-human animal The embryo is allowed to develop into a transgenic non-human animal and the VEGF-$A_{165}$ is capable of expressing in the lung bronchus epidermal cells of the transgenic non-human animal.

The present invention will further be illustrated by variable examples with reference made to the Figures.

EXAMPLE 1

Figure 1A:
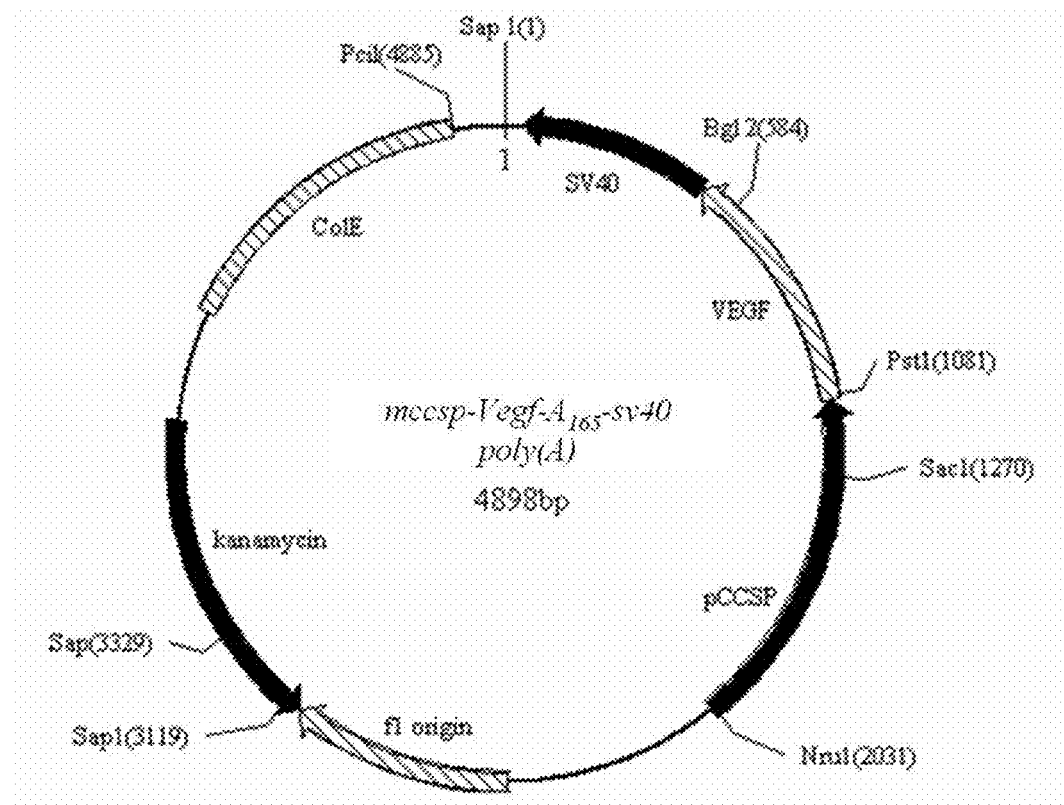
FIG. 1A is the outline map of mccsp-Vegf-$A_{165}$-sv40 poly (A) plasmid.
Figure 1B:
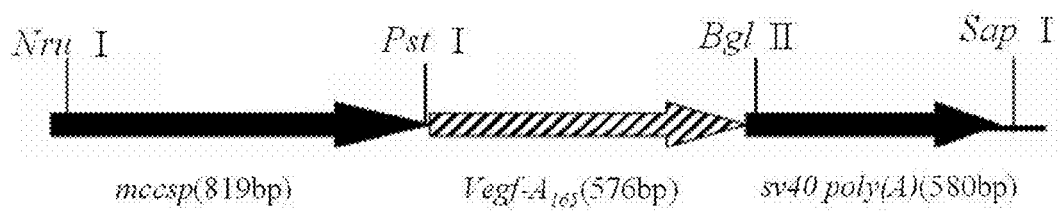
FIG. 1B is the linear map of the transgene.

Preparation of a Transgenic Mouse has a DNA Sequence of Transgene Encoding VEGF-$A_{165}$ The DNA sequence of transgene encoding VEGF-$A_{165}$ was constructed onto a site subsequent to a clara cell secretory protein (CCSP) promoter and then poly (A) sequence was subsequently connected to the VEGF-$A_{165}$ so as to form a lung-specific expression vector (CCSP-VEGF-$A_{165}$-sv40poly(A)) as shown in FIG. 1.

The lung-specific expression vector (2.0 kb) was purified and then the purified vector was introducing into an embryo of a mouse by a microinjection process. The embryo then was transplanted into a female mouse as a surrogate mother. Within 3 weeks after the embryo transfer, the transgenic mouse was born.

EXAMPLE 2

Selection of the Transgenic Mice

The transgenic mice produced in Example 1 were fed under a temperature-stable environment (25° C.). After they grew to the age about 1 month, a tail tissue of 1-2 cm was cut off per mouse to extract the DNA thereof. A polymerase chain reaction (PCR) was conducted to check whether or not each of the mice contains the transgene. The polymerase chain reaction used herein contains a primer as follows:

```
VEGF 94:      5'-AAGGAGGAGGGCAGAATCATC-3'
VEGF 315:     5'-GAGGTTTGATCCGCATAATCTG-3'
```

Figure 2:
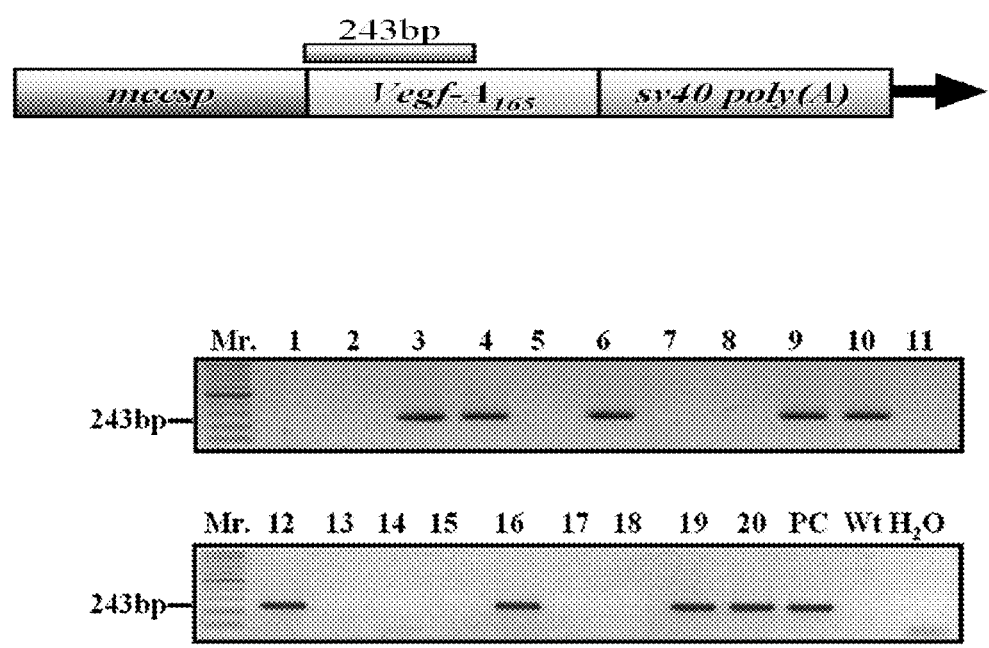
FIG. 2 is identification of the transgenic mice by PCR screening. The schema represents the position of the PCR product in the linear transgene. The PCR product is 243 bp. The results of PCR screening showed that there were 9 transgenic mice in the 20 screened mice.

The products were taken into 1.5% agarose gel electrophoresis analysis and the so-acquired results indicated that the PCR product was 243 base pairs. These results were shown in FIG. 2 and indicated that 9 mice of them (No. 3, 4, 6, 9, 10, 12, 16, 19, and 20) were truly the transgenic mice whose genomes respectively include the DNA sequence of transgene encoding VEGF-$A_{165}$.

EXAMPLE 3

Confirming that the Transcript Gene is Capable of Passing on to an Offspring by Sexual Reproduction Each of three transgenic mice (respectively named as $VEGF_{165}$-Tg-No. 1, $VEGF_{165}$-Tg-No. 2 and $VEGF_{165}$-Tg-No. 3) firstly produced was respectively matched to a wild type (Wt) mouse to produce its own offspring (F1, F2 and F3). The procedures described in Example 2 were repeated to sampling the tail tissues each of the offspring for conducting a PCR so as to select the mice having VEGF-$A_{165}$.

The results were shown in Table I wherein the denominator represented the total quantity of the mice in each generation and meant that it is the mice quantity conducted in the PCR analysis while the numerator represented the quantity of transgenic mice confirmed by PCR analysis.

TABLE I

| Generation No. | VEGF$_{165}$-Tg-No.1 | VEGF$_{165}$-Tg-No.2 | VEGF$_{165}$-Tg-No.3 |
|---|---|---|---|
| F1 | 5/16 | 7/25 | 16/52 |
| F2 | 19/36 | 13/21 | 25/52 |
| F3 | — | — | 31/42 |

From Table I, it is learned that the transgene is capable of stably passing on to its offspring by sexual reproduction process conducted on the transgenic mice.

EXAMPLE 4

Analyzing the Appearance of a Transgenic Mouse

In case of the transgenic mice with the age over 12 months, the mice were anesthetized by using avertin (tribromoethanol) and further were sacrificed. The chest of per mouse was cut open by scissors to make a comparison of the exterior of its lung with that of the Wt mouse. According to the injury level, three groups, Tg-level-1, Tg-level-2, and Tg-level-3, were divided.

Figure 3:
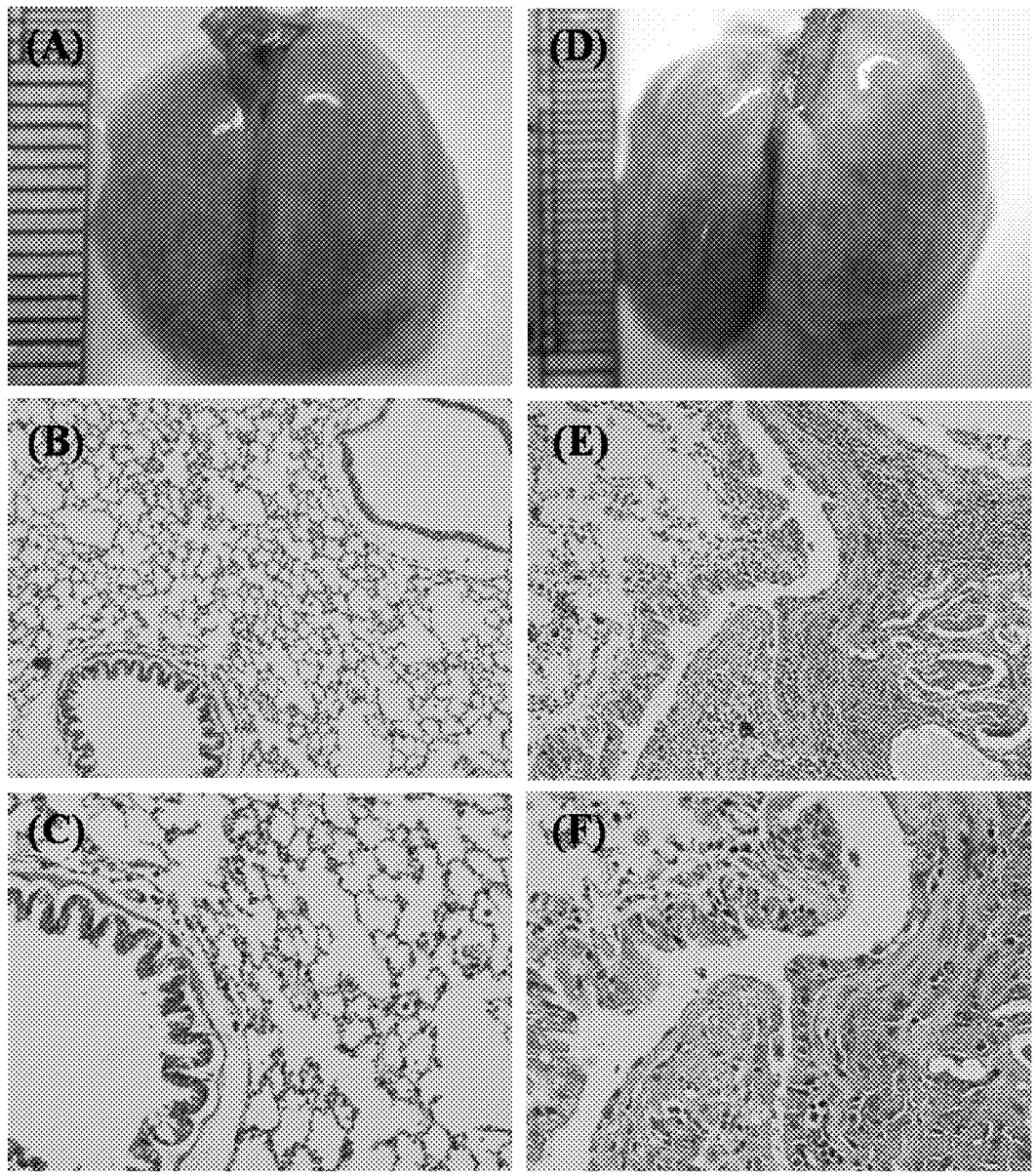
FIG. 3A shows the exterior of the lung in the Wt mice.
FIG. 3B is the bronchia and alveoli of the lung tissue in the Wt mice.
FIG. 3C is 2× magnification of the FIG. 3B.
FIG. 3D shows the exterior of lung in the Tg-level-1 transgenic mice.
FIG. 3E is he proliferation of the cells on the bronchial epithelium and the cyst on the bronchial epitheliumthe in the Tg-level-1 transgenic mice.
FIG. 3F is 2× magnification of the FIG. 3E.
Figure 4:
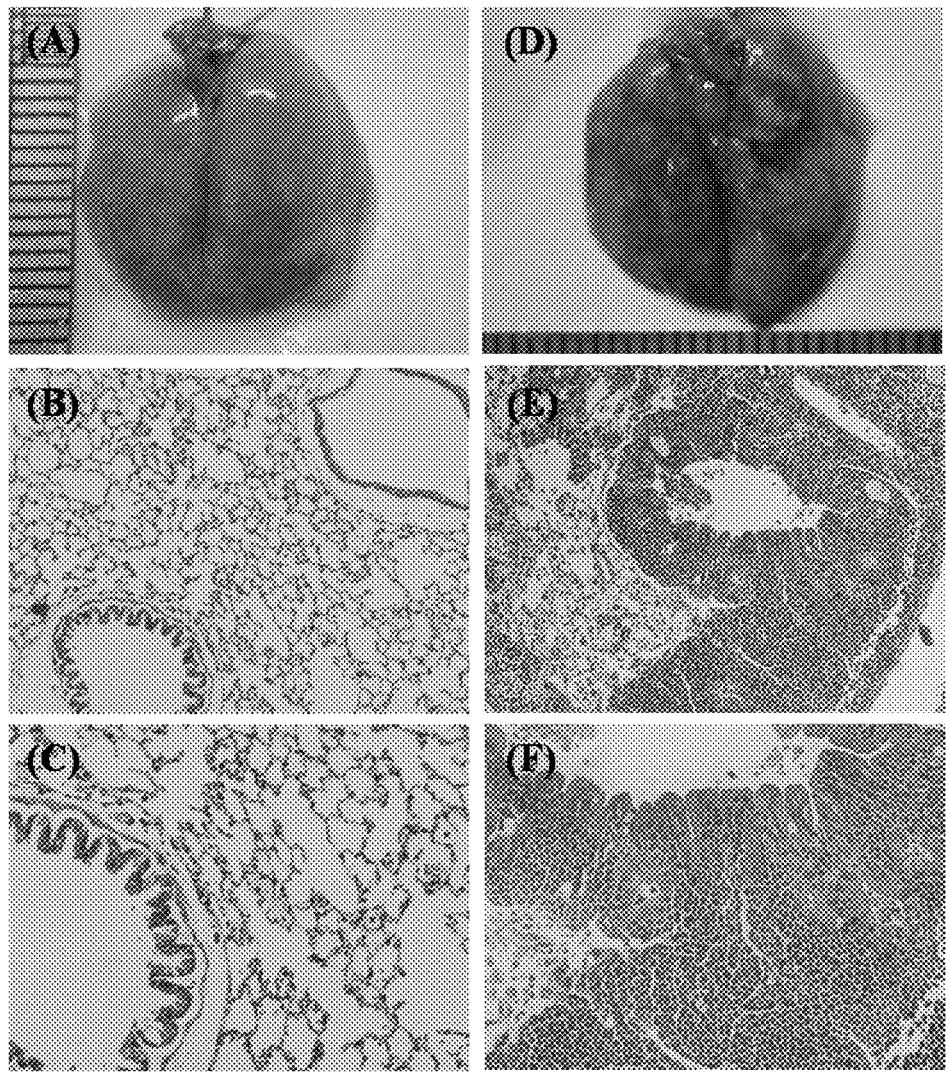
FIG. 4A shows the exterior of the lung in the Wt mice.
FIG. 4B is the bronchia and alveoli of the lung tissue in the Wt mice.
FIG. 4C is 2× magnification of the FIG. 4B.
FIG. 4D shows the exterior of lung in the Tg-level-2 transgenic mice.
FIG. 4E is the inflammation of the bronchial epithelium and the alveoli in the Tg-level-2 transgenic mice.
FIG. 4F is 2× magnification of the FIG. 4E.
Figure 5:
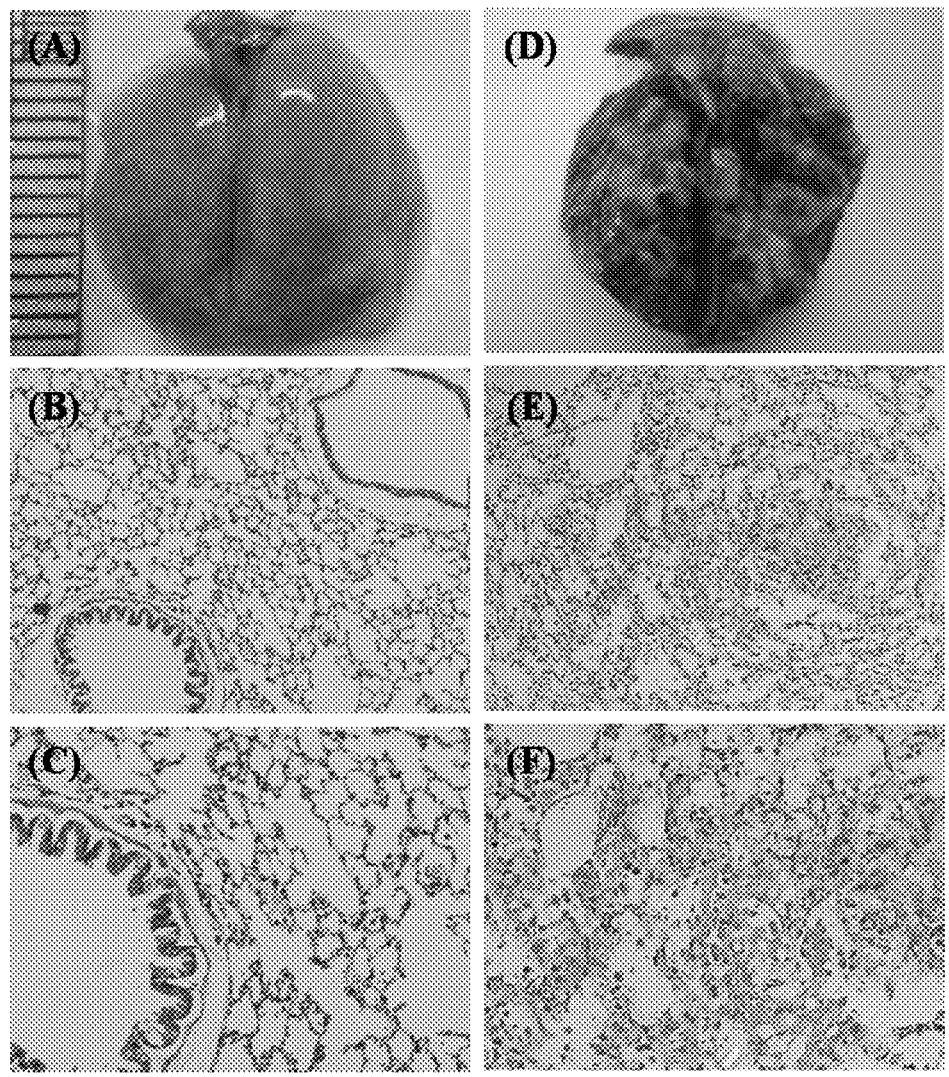
FIG. 5A shows the exterior of lung in the Wt mice.
FIG. 5B is the bronchia and alveoli of the lung tissue in the Wt mice.
FIG. 5C is 2× magnification of the FIG. 5B.
FIG. 5D shows the exterior of the lung in the Tg-level-3 transgenic mice.
FIG. 5E is the neoplasm in the alveoli of the Tg-level-3 transgenic mice.
FIG. 5F is 2× magnification of the FIG. 5E.
Figure 6:
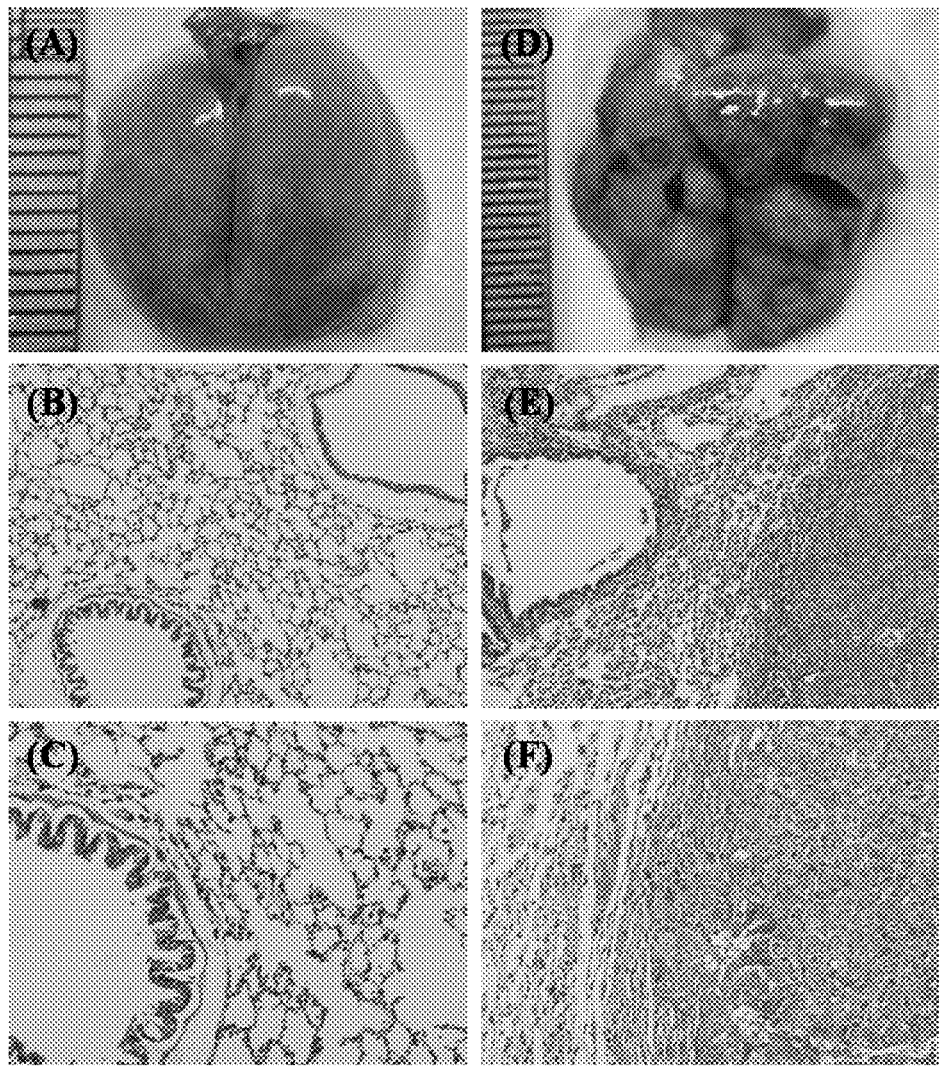
FIG. 6A shows the exterior in lung of the Wt mice.
FIG. 6B is the bronchia and alveoli of the lung tissue in the Wt mice.
FIG. 6C is 2× magnification of the FIG. 6B.
FIG. 6D shows the exterior of the lung in the Tg-level-3 transgenic mice.
FIG. 6E is the bronchia, alveoli and adenomas of the lung tissue in the Tg-level-3 transgenic mice.
FIG. 6F is 2× magnification of the FIG. 6E.

The Tg-level-1 transgenic mice had the exterior of the lung tissues without obvious difference (shown in FIG. 3D). The lung tissues of the Tg-level-2 transgenic mice had the exterior of red color block distribution (shown in FIG. 4D). The lung tissues of the Tg-level-3 transgenic mice had an exterior of serious injure and had a formed tumor protrusion (shown in FIG. 5D and FIG. 6D).

EXAMPLE 5

Figure 7:
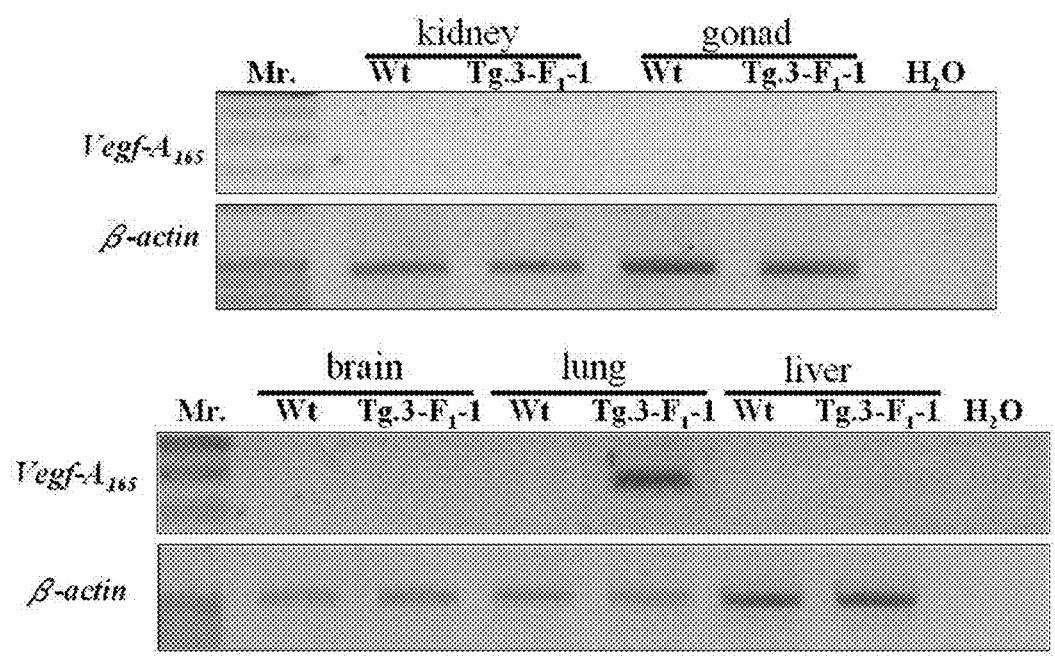
FIG. 7 is the schematic representation of Vegf-$A_{165}$ mRNA expression status in different tissues each of the transgenic mice by semi-quantitative RT-PCR. The RT-PCR of β-actin was used as an internal control.

Analyzing on the Specific Expression of VEGF-A$_{165}$ mRNA to Lung of a Transgenic Mouse Extract different tissues mRNA of each transgenic mouse for conducting a semi-quantitative reverse transcriptase-PCR (RT-PCR) and the results were reported in FIG. 7 showing that VEGF-A$_{165}$ mRNA had exact expression specific to the lung of the mouse while the VEGF-A$_{165}$ mRNA was not found in the tissues of other organs including, for example, kidney, gonad, brain, liver and so on. It was also shown was that the CCSP regulatory sequence was a promoter having an expression highly specific to the clara cells and was suitable for establishing an animal model of expressing the transgene specific to its lung.

EXAMPLE 6

Analyzing Sections of the Lung Tissue of a Transgenic Mouse

A central section of the lung tissue each of Tg-level-1, Tg-level-2 and Tg-level-3 transgenic mice was immersed into 4% paraformaldehyde for 24 hours to allow the tissue section was solidified. The tissue section then was modified by a knife into a suitable section and was sent to embed in paraffin. The paraffin embedded tissue block then was sent to slice by an automatic slicing machine for embedded block. After slicing, the slice had a thickness of 5 μm and was attached to a slide associated with poly-L-lysine. Then, the slice was treated to take off the paraffin and to recover water. And hematoxylin and eosin (H&E) was used to conduct tissue staining. As shown in FIG. 3 to FIG. 6, a comparison made of the resulted slice with the lung tissue slice from the Wt mice.

The exterior of the epidermal cells in the lung bronchus of the Wt mice was with a protrusion in a wave-like form (shown in FIG. 3B and FIG. 3C).

A cyst created by hyperplasia of the epidermis on the lung bronchus of the Tg-level-1 transgenic mice and by blockage of the secretory tissues further induced pulmonary emphysema. In addition, both local cell hyperplasia and flattening phenomena on the epidermis of the lung bronchus of a Tg-level-1 transgenic mouse were found. Cell flattening phenomenon is a phenomenon that the cell returns back to its primary status and has a potential of carcinogenesis (shown in FIG. 3E and FIG. 3F).

In pulmonary alveolus on lung bronchus of the Tg-level-2 transgenic mice, some obvious and large-grained pink cells were found. Such pink cells were macrophages indicating that there was obvious inflammation response (shown in FIG. 4E and FIG. 4F).

Formation of lung tumor was found in the Tg-level-3 transgenic mice and primarily included neoplasm growing on the peripheral of pulmonary alveolus (shown in FIG. 5E and FIG. 5F), and adenomas growing on the site near the lung bronchus (shown in FIG. 6E and FIG. 6F).

The VEGF-A$_{165}$ is capable of promoting the vascular permeability and the effectiveness of the inflammation response. Thus, from the foregoing results, it is learned that the inflammation response is caused by over-expression of the VEGF-A$_{165}$.

EXAMPLE 7

Figure 8:
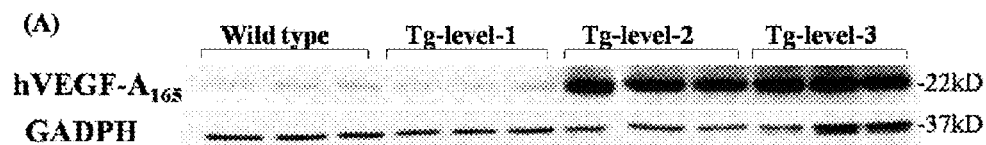
FIG. 8A is a schematic view showing the electrophoresis results acquired by conducting the western blotting method to VEGF-$A_{165}$. The western blot of GAPDH was used as an internal control.
FIG. 8B presents the quantitative VEGF-A165 protein expression level in FIG. 8A.
Figure 8:
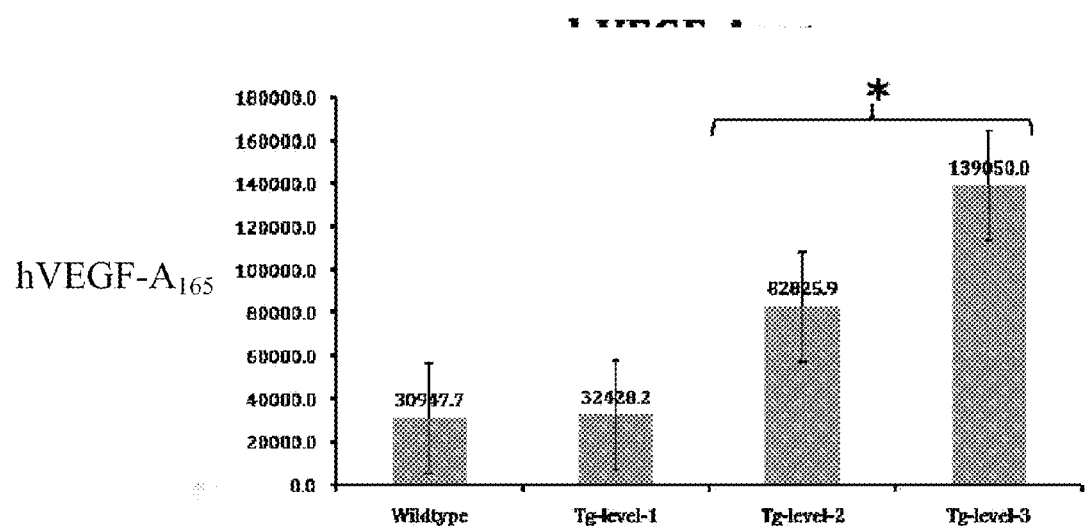

Analyzing the Expression of the VEGF-A$_{165}$ Protein on the Lung of a Transgenic Mouse Lung tissues each of the Tg-level-1, Tg-level-2 and Tg-level-3 transgenic mice were cut off to conduct polyacrylamide gel electrophoresis (SDS-PAGE) so as to divide the tissue proteins. After the electrophoresis, a primary antibody of VEGF-A$_{165}$ was used for detecting the VEGF-A$_{165}$ by western blotting. The results were shown in FIG. 8A.

From the results, it was indicated that the quantity of expression differed in terms of the lung exteriors and the slice levels of the transgenic mice. Comparing the quantity of the VEGF-A$_{165}$ protein of 22 kD with that of GAPDH protein of 37 kD (control group), it was learned that the quantity of the VEGF-A$_{165}$ protein expression of both the transgenic mice each of Tg-level-2 and Tg-level-3 was 2 times of that of the Wt mouse in the control group (shown in FIG. 8B).

By matching each expression resulted from the VEGF-A$_{165}$ protein to the lung tissue slices in each group, it was deemed that both the injuries and carcinomagenesis in the transgenic mice were positively related to the quantity of the VEGF-A$_{165}$ protein specific expression in the lung.

EXAMPLE 8

Figure 9:
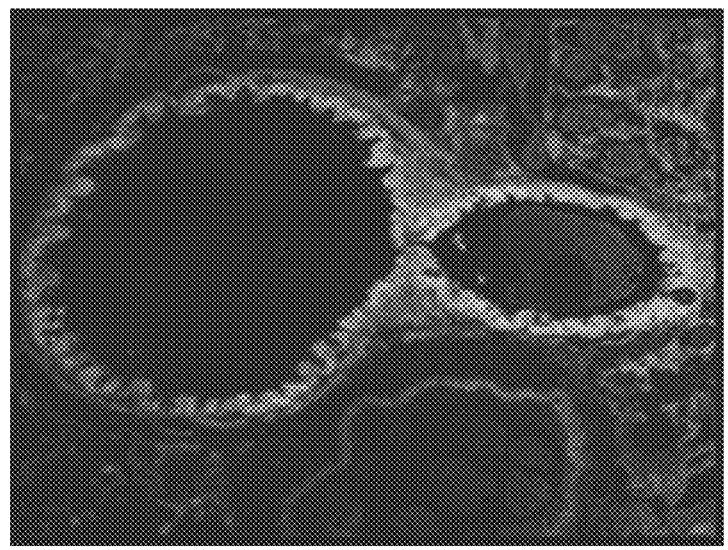
FIG. 9A shows the CCSP expressions in clara cells of the wild type mice observed from the immunohistochemistry process conducted thereto.
FIG. 9B shows the CCSP expressions in the clara cells each of the transgenic mice observed from the immunohistochemistry process conducted thereto.
Figure 9:
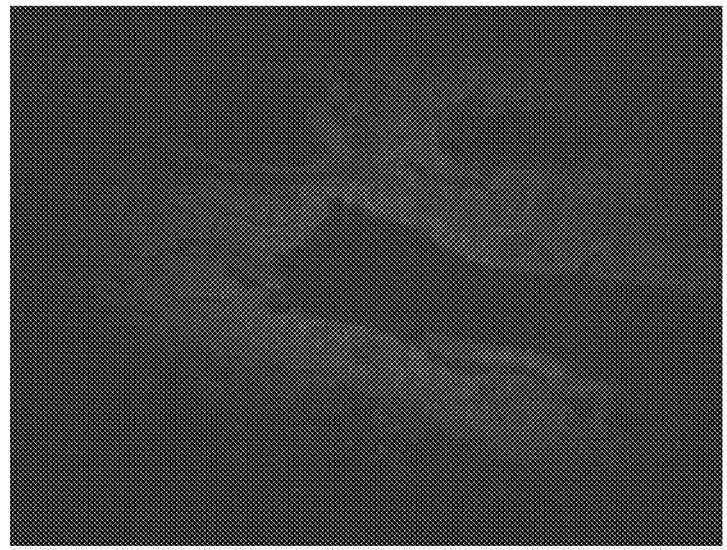

Investigating the VEGF-A$_{165}$ is Specific to the Clara Cell of a Transgenic Mice Slices from the sacrificed transgenic mice in Example 6 were taken into a test by utilizing the primary antibody of CCSP associated with a fluorescent label. The results acquired were shown in FIG. 9. As shown in FIG. 9, the expression of the fluorescent labeled CCSP was found in the bead-like calra cells on lung capillary bronchus slice of the Wt mice, while only very weak expression of the fluorescent labeled CCSP was found in that of the transgenic mice.

Figure 10:
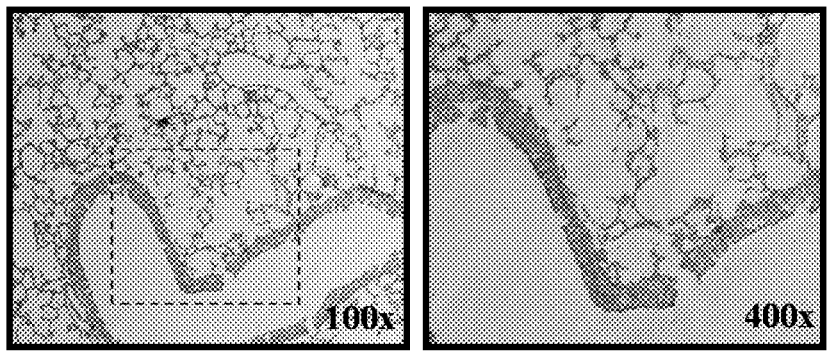
FIG. 10 shows exogenous hVEGF-$A_{165}$ expression assays by immunohistochemical (IHC) staining of the lung tissues of wild type and tumorigenesis transgenic mice.
Figure 10:
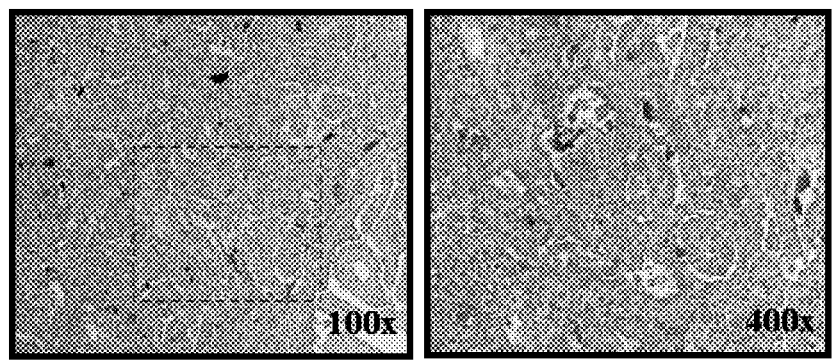

As shown in FIG. 10, from the results acquired from investigating the antibody of the VEGF-$A_{165}$ protein by utilizing immunohistochemistry, it was indicated that no VEGF-$A_{165}$ protein was detected in the slice of the Wt mice while obvious VEGF-$A_{165}$ protein was detected in the slice of the transgenic mice.

Based on the foregoing, exogenous human VEGF-$A_{165}$ protein was specifically expressed on the lung clara cells of the transgenic mice and the expression quantity of such protein in the transgenic mice was obviously higher than that in the Wt mice.

Based on the results from the foregoing examples, it was concluded that chronic inflammation or serious injuries and even the formation of a tumor toward carcinomagenesis phenomenon occurring in the lung of the transgenic mice aged 12 months or older were related both to the lung-specific VEGF-$A_{165}$ protein expression and the quantity of such expression.

Among current scientific studies, a common study procedure is to analyze the gene groups expressing in the transgenic animals or the gene-delete animals through utilizing variable statistic and selecting equipments and based on a bio-chip as database (Maiken et al., 2007). Thus, the differences regulated between the transgenic mice and the Wt mice in the present invention can further be investigated by utilizing cDNA microarray so as to confirm the adenocarcinoma-related mechanism in the animal model and to understand the adenocarcinomagenesis. Variable medicines, thus, can be taken into investigation base on the results so acquired.

The above-mentioned specification is only for detailedly describing the examples of the invention and shall not be construed as a limitation of the scope of the invention. Thus, any modification or change without departing from the characteristics of the invention or any equivalent thereof shall be included in the scope of the invention defined in the following claims.

What is claimed is:

1. A method for manufacturing a non-human animal model comprising the step of:
   a. constructing an expression vector encoding a VEGF-A gene operably linked to a clara cell secretory protein (CCSP) promoter; and
   b. introducing said expression vector into a non-human animal embryo and transplanting the embryo into a female non-human animal of the same species as the embryo;
      wherein said introducing step results in a transgenic non-human animal comprising in it genome said expression vector, said transgenic non-human animal expresses VEGF-A in epithelial cells of the bronchi and develops a pulmonary tumor.

2. The method of claim 1, wherein the non-human animal is a mouse.

3. A transgenic non-human animal whose genome comprises an expression vector encoding a VEGF-A gene operably linked to a CCSP promoter, wherein said transgenic non-human animal expresses VEGF-A in epithelial cells of the bronchi and develops a pulmonary tumor.

4. The transgenic non-human animal of claim 3, wherein the transgenic non-human animal is a mouse.

5. A transgenic non-human animal with development of an inflammatory response of infiltration of macrophages, whose genome comprising a transgenic gene comprising:
   a clara cell secretory protein promoter; and
   a DNA sequence of gene encoding a vascular endothelial growth factor A (VEGF-A) subsequently connected to said promoter.

6. The transgenic non-human animal of claim 5, wherein the transgenic non-human animal is a mouse.

* * * * *